United States Patent
Gizur et al.

(10) Patent No.: US 6,765,114 B1
(45) Date of Patent: Jul. 20, 2004

(54) PROCESS FOR THE SYNTHESIS OF 1-(AMINOMETHYL)CYCLOHEXYL-ACETIC ACID

(75) Inventors: Tibor Gizur, Budapest (HU); Zoltanné Lengyel, Budapest (HU); Krisztina Szalai, Budapest (HU)

(73) Assignee: Richter Gedeon Vegyeszeti Gyar RT., Budapest (HU)

( * ) Notice: Subject to any disclaimer, the term of this patent is extended or adjusted under 35 U.S.C. 154(b) by 0 days.

(21) Appl. No.: 09/856,517

(22) PCT Filed: Dec. 23, 1999

(86) PCT No.: PCT/HU99/00102

§ 371 (c)(1),
(2), (4) Date: May 21, 2001

(87) PCT Pub. No.: WO00/39074

PCT Pub. Date: Jul. 6, 2000

(30) Foreign Application Priority Data

Dec. 29, 1998 (HU) .............................. 9803034

(51) Int. Cl.$^7$ .......................... C07C 61/10; C07C 69/74
(52) U.S. Cl. ....................... 562/507; 560/126
(58) Field of Search .......................... 562/507; 560/126

(56) References Cited

U.S. PATENT DOCUMENTS

| | | | | |
|---|---|---|---|---|
| 3,253,039 A | * | 5/1966 | Rylander et al. ............. | 562/553 |
| 3,594,419 A | * | 7/1971 | Rosenthal ................... | 564/448 |
| 3,766,271 A | * | 10/1973 | Knifton ...................... | 564/448 |
| 4,024,175 A | * | 5/1977 | Satzinger et al. ........... | 424/305 |
| 4,894,476 A | * | 1/1990 | Butler et al. ................ | 562/504 |
| 5,091,567 A | | 2/1992 | Geibel et al. ............... | 562/507 |
| 5,095,148 A | | 3/1992 | Mettler et al. .............. | 562/507 |
| 5,130,455 A | | 7/1992 | Mettler et al. .............. | 558/426 |

FOREIGN PATENT DOCUMENTS

| | | | |
|---|---|---|---|
| EP | 0 414 263 | 2/1991 | |
| HU | 207 284 | 3/1993 | |
| WO | WO 99/21824 | 5/1999 | ......... C07C/229/28 |

OTHER PUBLICATIONS

C.a. vol. 108:74837 Org. Prep. Proced. Int (1987), 19(6), 471–5.

* cited by examiner

Primary Examiner—D. Margaret Seaman
Assistant Examiner—Taylor V Oh
(74) Attorney, Agent, or Firm—Herbert Dubno; Jonathan Myers

(57) ABSTRACT

The invention relates to a new process for the synthesis of 1-(aminomethyl)cyclohexyl-acetic acid of formula (I) via the new intermedier 1-(nitromethyl)cyclohexyl-acetic acid derivative of formula (II), wherein R represents hydrogen, benzyl group, diphenylmethyl group or $C_1$–$C_4$ alkyl or alkoxy aromatic ring substituted derivatives thereof.

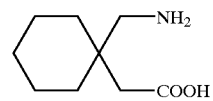

(I)

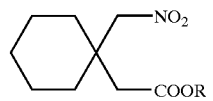

(II)

9 Claims, No Drawings

PROCESS FOR THE SYNTHESIS OF 1-(AMINOMETHYL)CYCLOHEXYL-ACETIC ACID

FIELD OF THE INVENTION

The invention relates to a new process for the synthesis of 1 (aminomethyl)cyclohexyl-acetic acid of the formula (I) via the new intermediate 1-(nitromethyl)cyclohexyl-acetic acid compound of formula (II), wherein R represents hydrogen, benzyl group, diphenylmethyl group or $C_1$–$C_4$ alkyl or alkoxy aromatic ring substituted derivative thereof.

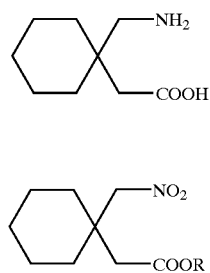

The 1-(aminomethyl)cyclohexyl-acetic acid of formula (I), otherwise known as gabapentin is the active ingredient of the GABA antagonist drug. Several methods are known from the literature for the synthesis of this compound.

BACKGROUND OF THE INVENTION

In most of the known methods an intermediate is hydrolyzed with acid, and gabapentin is obtained from the so formed gabapentin hydrochloride salt by using ion exchange resin. This process is described in the German patent No. DE 2 460 891, in which the 1,1-cyclohexyldiacetic acid anhydride is converted into hydroxamic acid and the latter is transformed via Lossen degradation into the hydrochloride salt of the product. The U.S. Pat. 4,024,175 describes a method where the same 1, 1-cyclohexyldiacetic acid anhydride is used as starting material. The anhydride is first transformed into a monoethyl ester monosalt and then a monoacid monoazide is obtained from it. The gabapentin hydrochloride is prepared from the latter via Curtius degradation.

Similarly gabapentin hydrochloride is formed in the procedure described in the European patent No. EP 414 274. According to this invention the alkyl ester of 1-(nitromethyl) acetic acid is transformed into a 2-aza-spiro[4,5]decane-3-on derivative by catalytic hydrogenation. The gabapentin hydrochloride is obtained from the latter lactam derivative by refluxing it with hydrochloric acid and gabapentin is isolated by using an ion exchange resin.

The disadvantages of the above mentioned procedures are as follows. The gabapentin is obtained as its hydrochloride salt and gabapentin itself can be isolated only by using labor-demanding and expensive ion-exchange methods. To avoid the unwanted lactam formation side-reaction requires also a labor-demanding and expensive technique. Further disadvantages of these procedures are the use of hazardous reagents, e.g. potassium cyanide, sodium azide and the expensive pressure resistant equipment. The procedure described in the European patent No. EP 414 275 avoids the formation of the lactam compound and the gabapentin hydrochloride, and in this way the use of the expensive ion-exchange method. According to this procedure cyano-cyclohexane-maleinic acid derivatives are hydrolyzed with base, decarboxylated and finally the nitrile group is catalytically hydrogenated. On the other hand this patent does not describe the synthesis of the cyano-cyclohexane-maleinic acid derivatives, which is a multi step, tedious process. It is important to note, that the synthesis of the maleinic acid ester is four steps starting from cyclohexanone, so the synthesis of gabapentin is altogether seven steps. The patent does not mention the purity of the obtained gabapentin either, in contrast to other patents, which describe the synthesis of gabapentin, e.g. EP 414 274.

OBJECT OF THE INVENTION

The object of the invention is to elaborate an economical, industrially applicable process for the synthesis of gabapentin, which eliminates the disadvantages of the above mentioned procedures and makes possible the simple synthesis of the very pure final product of formula (I) in fewer steps and in good yield.

SUMMARY OF THE INVENTION

The synthesis of gabapentin according to the process of the invention is as follows a) the alkyl ester of cyclohexylidene-acetic acid of general formula (VI)—wherein $R_2$ represents $C_1$–$C_4$ alkyl group—is transformed into the alkyl ester of 1-(nitromethyl) cyclohexyl-acetic acid of formula (V)—wherein the meaning of $R_2$ is as defined above— with nitromethane in the presence of a base, the latter is hydrolized with aqueous methanolic solution of potassium hydroxide and the obtained 1(nitromethyl) cyclohexyl-acetic acid of formula (IIa) is hydrogenated in a solvent in the presence of a catalyst to yield the desired product of formula (I), or

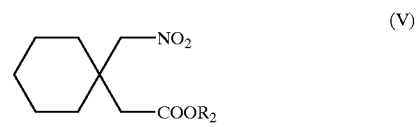

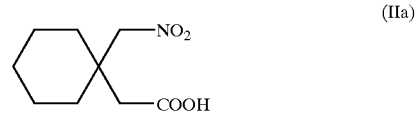

b) the alkyl ester of cyclohexylidene-acetic acid of general formula (VI)—wherein the meaning of R2 is as defined above—is hydrolyzed with aqueous methanolic solution of potassium hydroxide and the obtained cyclohexylidene-acetic acid of formula (IV) is reacted with a reagent of formula $R_1$-X—wherein $R_1$ represents benzyl group, diphenylmethyl group or in given case $C_1$–$C_4$ alkyl or alkoxy aromatic ring substituted derivatives thereof—to give the appropriate cyclohexylidene acid derivative of the general formula (III)—wherein the meaning of $R_1$ is as defined above—and this intermediate is transformed into a 1-(nitromethyl) cyclohexyl-acetic acid compound of the formula (IIb) wherein the meaning of $R_1$ is as defined above—with nitromethane and the latter is hydrogenated in a solvent in the presence of a catalyst.

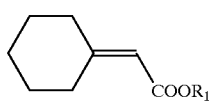
(III)

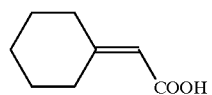
(IV)

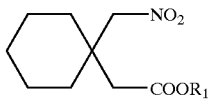
(IIb)

The process of the invention is illustrated on Scheme 1.

The invention based on the observation, that the reduction of the new compounds of the formula (II) at atmospheric pressure yields directly the pure desired final product.

Surprisingly it was found, that using the compounds of the formula (II) as starting materials in the reduction step the lactam compound is not formed, but the very pure gabapentin is obtained directly. This was not anticipated in the knowledge of previous procedures, as the ability of lactam formation of this type of compounds is known from the literature (e.g. EP 414 274).

The alkyl ester of cyclohexylideneacetic acid of the formula (VI) used as starting material can be prepared according to the literature via the reaction of cyclohexanone and the appropriate ester of diethylphosphono-acetic acid.

In the last hydrogenation step any catalysts can be used, which are generally applicable in hydrogenation reactions, rare metal catalysts, e.g. rhodium or palladium, Raney nickel or cobalt catalysts, in a given case on a carrier e.g. on carbon, preferably palladium on activated carbon, more preferably 10% of the compound to be reduced.

The hydrogenation is carried out in an inert organic solvent, preferably in a $C_1$–$C_4$ alcohol, more preferably in methanol, at 10–50° C., under 1–20 kPa pressure, preferably at room temperature and under atmospheric pressure.

The Michael addition of the ester of cyclohexylidene-acetic acid with nitromethane is carried out in the presence of a base, preferably potassium hydroxide.

The hydrolysis of the alkyl ester group is carried out with base, preferably aqueous methanolic solution of potassium hydroxide at room temperature; then the acid is liberated with 10% aqueous potassium dihydrogenphosphate solution.

After filtration of the catalyst the product is isolated by concentration of the filtrate. The product obtained on concentration is 98–99% pure, the yield is 50–70%. The advantages of this procedure are as follows:

the obtained product is very pure
the number of reaction steps is less than in the known procedures
the lactam compound, which is very difficult to remove, is not formed neither special pressure resistant equipment nor expensive catalyst is needed
the final product can be obtained without applying difficult and complicated ion-exchange technology
no poisonous or dangerous materials are needed

EXAMPLES

Example 1 a) Synthesis of 1-(nitromethyl)cyclohexyl-acetic Acid

A solution of 4.3 g (0.02 mol) of methyl 1-(nitromethyl) cyclohexyl-acetate in a mixture of 50 ml of methanol and 20 ml of 10% aqueous potassium hydroxide is stirred at room temperature for 24 h, then the methanol is distilled off in vacuo. The pH of the resulted aqueous solution is adjusted to 7 with 10% aqueous potassium dihydrogenphosphate solution. The solution is extracted three times with 30 ml of ethyl acetate, the combined organic layers are dried over sodium sulphate and concentrated to yield 32 g (80%) of the title compound as oil.

b) Synthesis of 1-(aminomethyl)cyclohexyl-acetic Acid

A solution of 2.01 g (0.01 mol) of 1-(nitromethyl)-cyclohexyl-acetic acid in 50 ml of methanol is hydrogenated in the presence of 0.2 g of palladium oil activated carbon at atmospheric pressure. The catalyst is filtered off and the filtrate is concentrated to 10 ml. 20 ml of tetrahydrofuran is added to the residue and the precipitated crystals were filtered off and dried to yield 1.3 g (80%) of the title compound. Mp: 164–169° C.

Example 2

Synthesis of 1-(aminomethyl)cyclohexyl-acetic Acid

A solution of 5 g (0.017 mol) of benzyl 1-(nitromethyl) cyclohexyl-acetate in 50 ml of methanol is added to a mixture of 0.5 g of prehydrogenated palladium, 10% on activated carbon in 50 ml of methanol. This mixture is hydrogenated at room temperature under atmospheric pressure until the calculated hydrogen is consumed, then the catalyst is filtered off, the filtrate is concentrated to about 15 ml and 30 ml of tetrahydrofuran is added to precipitate the title compound. Yield: 1.5 g (51%). Mp: 168° C.

What is claimed is:

1. A process for preparing pure 1-(aminoethyl)-cyclohexyl-acetic acid or a pharmaceutically acceptable salt thereof which comprises the steps of (a) catalytically hydrogenating a compound of the Formula (II)

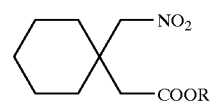
(II)

wherein
R is hydrogen, benzyl or diphenylmethyl or aryl which is unsubstituted or substituted by a $C_1$ to $C_4$ alkyl or alkoxy group in the presence of a hydrogenation catalyst in an inert organic solvent at a temperature of 10 to 50° C. under 1 to 20 kPa pressure to directly obtain the 1-(aminomethyl)-cyclohexyl-acetic acid in the inert organic solvent;

(b) filtering the 1-(aminomethyl)-cyclohexyl-acetic acid in the inert organic solvent prepared according to step (a) to remove the hydrogenation catalyst to obtain a filtrate;

c) concentrating the filtrate by removing a portion of the inert organic solvent to obtain pure 1-(aminomethyl)-cyclohexyl-acetic acid; and (d) in the case where a pharmaceutically acceptable salt is to be formed transforming the pure 1-(aminomethyl)-cyclohexyl-acetic acid into a pharmaceutically acceptable salt.

2. The process defined in claim 1 which further comprises the step of adding tetrahydrofuran to the concentrated filtrate obtained according to step c) to precipitate out pure 1-(aminomethyl)-cyclohexyl-acetic acid.

3. The process defined in claim 1 wherein according to step (a) the hydrogenation catalyst is palladium on activated carbon.

4. The process defined in claim 1 wherein according to step (a) the inert organic solvent is a $C_1$ to $C_4$ alcohol.

5. A compound of the Formula (II)

(II)

wherein

R is hydrogen, benzyl or diphenylmethyl or an aryl group which is unsubstituted by a $C_1$ to $C_4$ alkyl or alkoxy group.

6. 1-(nitromethyl)cyclohexyl-acetic acid as defined in claim 5.

7. Benzyl 1-(nitromethyl)-cyclohexyl-acetate as defined in claim 5.

8. Diphenylmethyl 1-(nitromethyl)-cyclohexyl-acetate as defined in claim 5.

9. The process defined in claim 1 wherein according to step (a) the hydrogenation catalyst in a rare metal, Raney nickel or cobalt.

* * * * *